United States Patent
Arakawa et al.

[11] Patent Number: 5,972,473
[45] Date of Patent: *Oct. 26, 1999

[54] SEPARATOR OR PACKAGING MATERIAL HAVING A MATTE OR EMBOSSED SURFACE

[75] Inventors: Masaaki Arakawa; Teiji Sakashita, both of Osaka, Japan

[73] Assignee: Nitto Denko Corporation, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/764,917

[22] Filed: Dec. 16, 1996

Related U.S. Application Data

[63] Continuation of application No. 08/334,377, Nov. 3, 1994, abandoned.

[30] Foreign Application Priority Data

Nov. 4, 1993 [JP] Japan ................................. 5-275476

[51] Int. Cl.$^6$ ..................................................... A61F 13/60
[52] U.S. Cl. ............................. 428/141; 28/173; 28/152; 28/156; 28/357; 28/220; 28/409; 28/40.1; 28/41.8; 28/42.2; 604/386; 604/387; 604/390
[58] Field of Search ..................................... 428/173, 152, 428/141, 156, 352, 220, 409, 40.1, 41.8, 42.2; 604/386, 387, 390

[56] References Cited

U.S. PATENT DOCUMENTS

| | | | |
|---|---|---|---|
| 4,279,717 | 7/1981 | Eckberg et al. | 204/159.13 |
| 4,452,840 | 6/1984 | Sato et al. | 428/156 |
| 4,772,512 | 9/1988 | Nagafuchi | 428/331 |
| 4,925,728 | 5/1990 | Crass et al. | 428/216 |
| 4,971,854 | 11/1990 | Hinishi et al. | 428/195 |
| 5,134,012 | 7/1992 | Arakawa et al. | 428/152 |
| 5,259,902 | 11/1993 | Muckenfuhs | 156/164 |
| 5,266,372 | 11/1993 | Arakawa et al. | 428/40 |
| 5,310,601 | 5/1994 | Riding | 428/428 |
| 5,369,205 | 11/1994 | Eckberg et al. | 528/25 |
| 5,376,420 | 12/1994 | Yamamoto et al. | 428/40 |
| 5,401,547 | 3/1995 | Blackwell et al. | 428/40 |

FOREIGN PATENT DOCUMENTS

| | | |
|---|---|---|
| 0150950 | 8/1985 | European Pat. Off. . |
| 0219198 | 4/1987 | European Pat. Off. . |
| 0448872 | 10/1991 | European Pat. Off. . |
| 2501577 | 9/1982 | France . |
| 324949 | 2/1991 | Japan ................. B32B 27/00 |
| 3184543 | 8/1991 | Japan ................. A61F 13/15 |
| 4115944 | 4/1992 | Japan . |
| 82 01861 | 6/1982 | WIPO . |
| 94 24977 | 11/1994 | WIPO . |

OTHER PUBLICATIONS

Derwent Publication No. AN 92–179533; Abstract of JP–A 04–115944.

*Primary Examiner*—William P. Watkins, III
*Attorney, Agent, or Firm*—Sughrue, Mion, Zinn, Macpeak & Seas, PLLC

[57] ABSTRACT

A separator or a packaging material is provided, comprising a thermoplastic plastic film at least one surface of which is a matte surface or an embossed surface having a surface roughness (Ra) of not larger than ½ of the thickness of the film. The thermoplastic film may have a release treatment layer on the whole or part of a surface. The separator or packaging material is useful as a separator for pressure-sensitive adhesive articles and disposable articles or as a packaging material for packing foods, pressure-sensitive adhesive articles and sanitary articles. In particular, the separator is suitably used as a separator for a disposable diaper and a sanitary napkin, and also the packaging material is suitably used as a package for a sanitary napkin.

14 Claims, 2 Drawing Sheets

SEPARATOR OR PACKAGING MATERIAL HAVING A MATTE OR EMBOSSED SURFACE

This is a Continuation of application Ser. No. 08/334,377 filed Nov. 3, 1994, abandoned.

FIELD OF THE INVENTION

The present invention relates to a separator for pressure-sensitive adhesive articles such as a pressure-sensitive adhesive sheet, a (double-sided) pressure-sensitive adhesive tape, a tack, etc., and for disposable articles such as a paper diaper, a napkin. etc., or a packaging material being used for packing foods, pressure-sensitive adhesive articles such as pressure-sensitive adhesive tacks, etc., and sanitary articles such as a sanitary napkin, etc. In particular, the separator of the present invention is suitably used as a separator for a disposable diaper and a sanitary napkin and also the packaging material of the present invention is suitably used as a package for a sanitary napkin.

BACKGROUND OF THE INVENTION

Hitherto, as separators for disposable articles such as, for example, disposable diapers and napkins and as packaging materials for sanitary articles such as sanitary napkins, etc., various materials are used. For example, as a packaging material for a napkin, a releasing tape and a packaging material each comprising a substrate composed of a flexible plastic film having thereon a releasing agent layer are proposed as described, e.g., in JP-A-3-24949 and JP-A-3-184543 (the term "JP-A" as used herein means an "unexamined published Japanese patent application"). However, the substrates used for the foregoing materials are plastic films each composed of a single component, such as polyethylene, polypropylene, polyester, nylon, cellophane, etc., and hence there is a problem that the substrate is too soft or, to the contrary, too hard.

That is, if the substrate is too soft, the substrate is stretched or cut in the conveying step in the production line of napkins, etc., which results in greatly lowering the productivity. Also, if the substrate is too hard, the product such as the releasing tape and the packaging material has a disadvantage that a soft feeling from the point of the practical use is lost and the releasing sound becomes large to lower the commercial value thereof.

Furthermore, from the productivity, when the release treatment surface of the film is smooth, the static friction coefficient and the kinetic friction coefficient become large, whereby the friction at the contact of the film with rolls in the step of producing or packaging articles such as pressure-sensitive adhesive articles and sanitary articles is increased to fall off the releasing agent and cut the film, which become the cause of troubles.

SUMMARY OF THE INVENTION

As the result of various investigations for solving the problems described above, the inventors have discovered that by applying specific working to the surface of a plastic film as the substrate or forming the film as the substrate with a polymer blend, a separator or a packaging material wherein the foregoing problems are solved and which can be very practically used can be obtained and have succeeded in achieving the present invention based on the foregoing discovery.

That is, according to the present invention, there is provided a separator or a packaging material comprising a thermoplastic plastic film at least one surface of which is a matte surface or embossed surface having a surface roughness (Ra) of not larger than ½ of the thickness of the film.

DETAILED DESCRIPTION OF THE INVENTION

Figure 1:
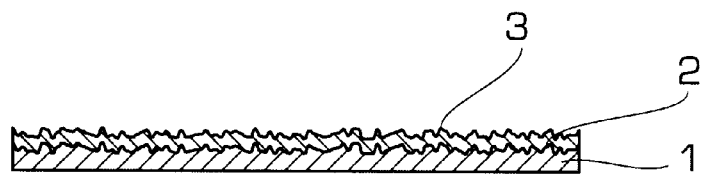
FIG. 1 is a cross sectional view showing an example of the separator of the present invention.

Then, the present invention is described in detail.

In the present invention, one surface or both the surfaces of the thermoplastic plastic film as the substrate is formed such that the surface becomes a matte surface or an embossed surface and the surface has a surface roughness (Ra) of not larger than ½, and preferably from ¼ to ¹⁄₁₀ of the thickness of the film. By making the surface roughness (Ra) of the substrate in the range described above, the friction coefficient can be reduced, which is effective for the smooth conveyance and the improvement of the speed of the plastic film in the line of producing or packaging the articles mentioned above and further for the stabilization of the releasing property from a pressure-sensitive adhesive layer of the articles. In this case, the surface roughness (Ra) is the value obtained by the method described hereinafter.

Also, the thickness of the thermoplastic plastic film is preferably not thicker than 50 μm, and particularly preferably from 20 to 40 μm. If it is too thick, the mechanical strength becomes small, providing a disadvantage in workability on machining and there exists a possibility that cutting of the film occurs on handling at a practical use. Taking the above into account, the surface roughness (Ra) of the matte surface or embossed surface is generally 25 μm or less, preferably approximately from 2 to 10 μm.

The present invention provides a separator or a packaging material comprising the foregoing thermoplastic plastic film as the substrate, which is a single layer and composed of a polymer blend, at least one surface of said film being a matte surface or an embossed surface by the polymer blend.

Now, the polymer blend constituting the thermoplastic plastic film is composed of a composite resin of at least 2 kinds selected from polyethylene, polypropylene, an ethylene-vinyl acetate copolymer, an ethylene-(meta)acrylic acid copolymer, an ethylene-methyl (meta)acrylate copolymer, an ethylene-ethyl (meta)acrylate copolymer, a polyethylene-propylene copolymer, an olefinic elastomer, a styrenic elastomer, polyisobutyrene, and butyl rubber. In this case, as the olefinic elastomer, there are an ethylene-propylene rubber (EPT), an ethylene-propylene-diene rubber (EPDM), an ethylene-propylene series elastomer, an ethylene-butene series elastomer, etc. As the styrenic elastomer, there are a styrene-isoprene-styrene block copolymer (SIS), a styrene-butadiene-styrene block copolymer (SBS), etc., and the hydrogenated products of them. Preferred examples of the polymer blend include a blend of polyethylene/polypropylene (the weight ratio: 9/1 to 5/5), a blend of polyetylene/EVA/polypropylene (the weight ratio: 9/0.5/0.5, 8/1/1, 7/1/2, 7/2/1, 6/2/2, 5/3/2, 5/2/3, and 4/3/3), and a blend of polyethylene/copolymer of polyethylene and polypropylene (elastomer)/polypropylene (the weight ratio: 9/0.5/0.5, 8/1/1, 7/1/2, 7/2/1, 6/2/2, 5/3/2, 5/2/3, and 4/3/3).

In the present invention, such polymers are blended and in this case, it is considered that when the polymers having poor compatibility with each other are blended, since they are mixed in the state of being separated from each other by the difference in their surface tensions at a dissolved state, uniform mixing of the polymers is not obtained in the surface state to roughen the surface without giving a smooth surface, whereby the surface becomes a matte surface or an embossed surface.

As the method of forming a film of the polymer blend, conventional methods such as a T die method and an inflation method may be used.

Furthermore, by blending the polymers each having different characteristics, it becomes possible to obtain a polymer blend having the merits of each polymer, which gives an effect that a polymer blend having a new function, for example, a function having simultaneously a softness and a nerve can be obtained.

Also, by blending relatively soft polymers and/or elastomers as described above, the effect that at releasing for use, the releasing sound can be lowered and thus the use of it is not perceived by others.

Furthermore, as other method of forming the matte surface or the embossed surface in the present invention than the polymer blending method described above, the matte surface or the embossed surface can be formed by contacting a roll surface to the surface at the production of the film, for example, after extruding the film through a T die. When the embossed surface is formed in the present invention, the latter method is more preferred.

Moreover, in the present invention, the thermoplastic plastic film can be constituted by a multilayer plastic film such as a double layer film, a 3 layer film, a 4 layer film, etc., and at least one surface of the multilayer thermoplastic plastic film can be formed by a matte surface or an embossed surface composed of the polymer blend described above. By employing such a multilayer structure, there is a merit that the characteristics of the polymer film of each layer can be combined as the case of the polymer blend, whereby a new function such as, for example, a function of simultaneously improving the tear resistance and the improvement of the feeling can be added.

There is no particular restriction on the polymers being used for other layer(s) than the matte surface or the embossed surface composed of the polymer blend in such a multilayer thermoplastic plastic film, but as such polymers, there are, for example, polyethylene, polypropylene, an ethylene-vinyl acetate copolymer, an ethylene-(meta)acrylic acid copolymer, an ethylene-methyl (meta)acrylate copolymer, an ethylene-ethyl (meta)acrylate copolymer, and a polyethylene-propylene copolymer. Also, there are composite resins of two or more kinds of polymers selected from polyethylene, polypropylene, an ethylene-vinyl acetate copolymer, an ethylene-(meta)acrylic acid copolymer, an ethylene-methyl (meta)acrylate copolymer, an ethylene-ethyl (meta)acrylate copolymer, a polyethylene-propylene copolymer, an olefinic elastomer, a styrenic elastomer, polyisobutyrene, and butyl rubber.

Furthermore, in the present invention, it is preferred that at least one surface of the thermoplastic plastic film has a release treatment layer on the whole surface or on a part of the surface. By forming such a release treatment layer, there is the effect that the surface of a pressure-sensitive adhesive layer of the articles can be protected and by partially forming the release treatment layer, the releasing force of the film from a pressure-sensitive adhesive layer of the articles can be controlled.

As the embodiment of the present invention, there is, for example, a separator or a packaging material comprising a thermoplastic plastic film one surface of which is a matte surface or an embossed surface having a surface roughness (Ra) of not larger than ½ of the thickness of the plastic film and other surface of which has a release treatment layer.

As other embodiment of the present invention, there is a separator or a packaging material comprising a thermoplastic plastic film one surface of which is a matte surface or an embossed surface having a surface roughness (Ra) of not larger than ½ of the thickness of the plastic film and having on the matte surface or the embossed surface a release treatment layer.

In this case, the static friction coefficient of the release treated matte surface or embossed surface is less than 1.5, and preferably from 0.4 to 1.0 and the kinetic friction coefficient of the surface is preferably less than 1.2, and preferably from 0.2 to 0.7. By selecting the friction coefficients in the ranges, there are the effects that the running property of the plastic film in the line of producing or packaging the articles can be improved and also at the contact with rolls, creases, zigzagging, and cutting are reluctant to occur.

For such a release treatment layer, a long chain alkyl series release treatment agent and a silicone series release treatment agent are used, and the silicone series release treatment agent can be properly selected from a thermosetting type release treatment agent, a ultraviolet setting type release treatment agent, an electron ray setting release treatment agent, etc. The release treatment layer can be form on the whole surface or a part of the surface such as both dry edges, patterns, the center portion, etc.

Also, when the separator or the packaging material of this invention is used as a separator or a package for a napkin, the sound caused by releasing it from the napkin, at folding the separator by hands, and at breaking the package can be lowered and in the present invention, the sound pressure level can be reduced, for example, to 80 dB or less.

Then, the invention is explained by referring to the accompanying drawings.

FIG. 1 to FIG. 4 are cross sectional views each showing an example of the separator of the present invention.

In FIG. 1, one surface of a thermoplastic plastic film 1 is a matte surface (or embossed surface) 2 and a release treatment layer 3 is formed on the surface of the matte surface (or embossed surface) 2.

Figure 2:
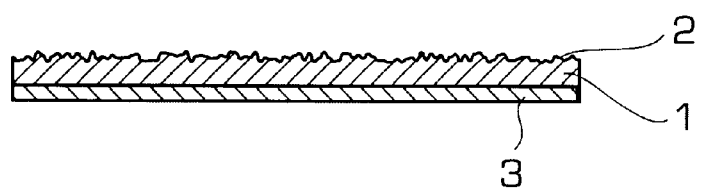
FIG. 2 is a cross sectional view showing other example of the separator of the present invention.

In FIG. 2, one surface of a thermoplastic plastic film 1 is a matte surface (or embossed surface) 2 and a release treatment later 3 is formed on the other surface of the film 1.

Figure 3:
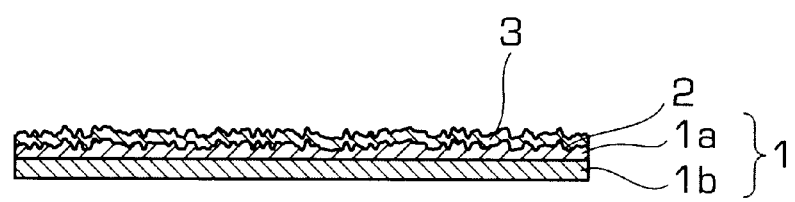
FIG. 3 is a cross sectional view showing still other example of the separator of the present invention.

In FIG. 3, the surface of a 1st layer (1a) of a thermoplastic plastic film 1 composed of double layers (1a and 1b) is a matte surface (embossed surface) 2 and the release treatment layer 3 is formed on the surface of the matte surface (embossed surface) 2.

Figure 4:
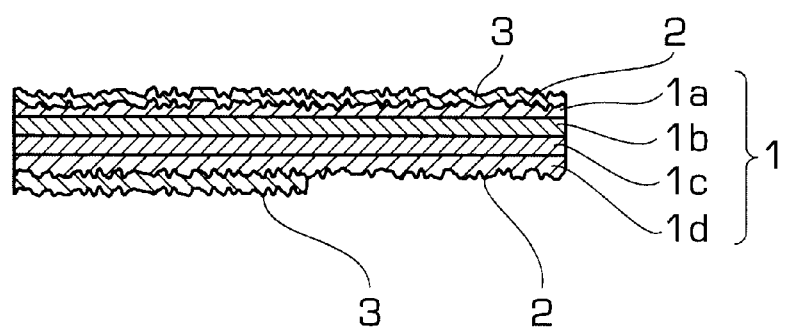
FIG. 4 is a cross sectional view showing another example of the separator of the present invention.

In FIG. 4, the surface of a 1st layer (1a) of a thermoplastic plastic film 1 composed of 4 layers (1a, 1b, 1c and 1d) is a matte surface (embossed surface) 2, a release treatment layer 3 is formed on the whole surface of the matte surface (embossed surface) 2, the surface of the 4th layer (1d) of the plastic film is also a matte surface (embossed surface) 2, and a release treatment layer 3 is formed at a part of the matte surface (embossed surface) 2.

Figure 5:
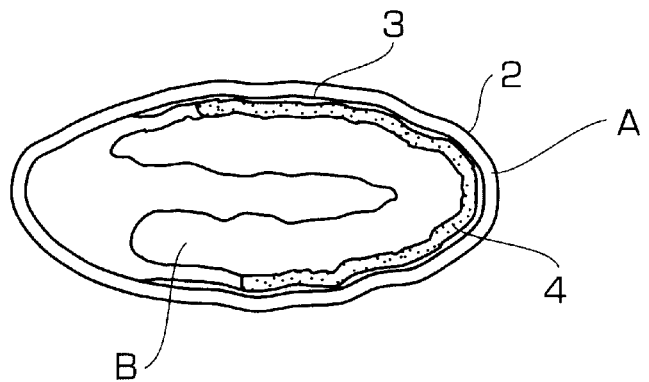
FIG. 5 is a schematic view showing the case of using the packaging material of the present invention for packing a napkin.
Figure 6:
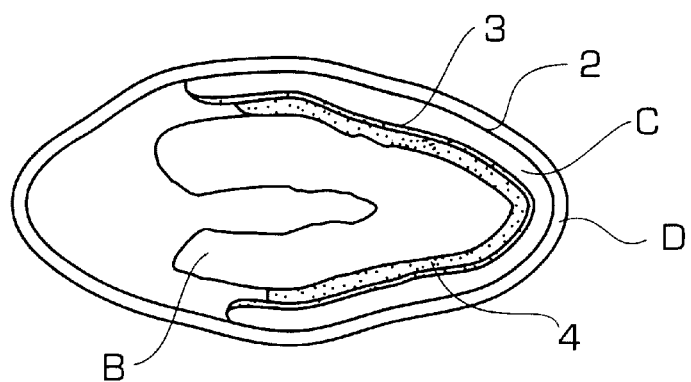
FIG. 6 is a schematic view showing the case of using the separator of the present invention for packing a napkin.
Figure 7:
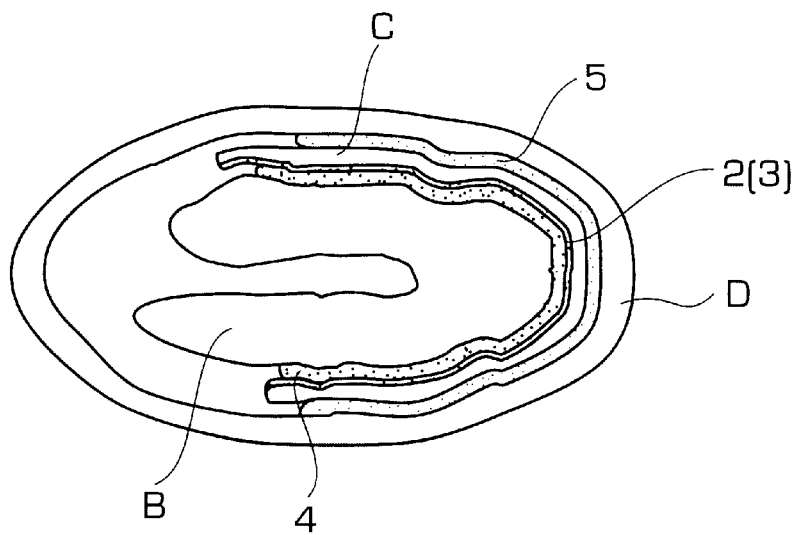
FIG. 7 is a schematic view showing other case of using the separator of the present invention for packing a napkin.

FIG. 5 to FIG. 7 are schematic views each showing the case of using the separator or the packaging material of the present invention as a package for a napkin.

In FIG. 5, a package A is composed of the packaging material of the present invention, the outside surface of the package is a matte surface 2, and the package has a release treatment layer 3 on the inside surface thereof, i.e., the side facing a pressure-sensitive adhesive layer 4 of a napkin. In the inside of the package A, a napkin B is placed and fixed via the pressure-sensitive adhesive layer 4.

In FIGS. 6 and 7, a pressure-sensitive adhesive layer 4 formed on a napkin B is protected with the separator C of the present invention and they are placed in a package D. In FIG. 6, the outside surface of the separator C is a matte surface 2 and on the inside surface thereof, i.e., the side facing the pressure-sensitive adhesive layer 4 is formed a release treatment layer 3. Also, in FIG. 7, the separator C is placed and fixed in the package D through other pressure-sensitive adhesive layer (e.g., a hot melt type pressure-sensitive adhesive layer) 5. Also, the separator C can be fixed by heat seal. In this embodiment, the inside surface of the separator C, i.e., at the side facing the pressure-sensitive adhesive layer is a matte surface and forms a release treatment layer 3.

Then, the invention is described in more detail by the following examples.

EXAMPLE 1

A double layer plastic film (thickness 25 $\mu$m) composed of a blend polymer layer (thickness 5 $\mu$m) composed of 70% by weight polyethylene, 20% by weight polypropylene, and 10% by weight a polyethylene-propylene copolymer as a 1st layer, the surface of which was a matte surface, and a polypropylene single layer (thickness 20 $\mu$m) as a 2nd layer was prepared and a release treatment layer was formed by coating the matte surface with a non-solvent silicone to provide the separator of the present invention. The surface roughness of the release treated matte surface was 3 $\mu$m.

EXAMPLE 2

A film of 20 $\mu$m in thickness was formed by extruding a polymer blend composed of 50% by weight polyethylene, 45% by weight polypropylene, and 5% by weight the hydration product of a styrene-isoprene-styrene block copolymer (SIS) and directly after extruding, the surface of the film was brought into contact with an embossing roll having a surface roughness of 10 $\mu$m to form an embossed surface having a surface roughness of 10 $\mu$m on one surface of the film. Then, a release treatment layer was formed on the embossed surface by coating the surface with a ultraviolet ray setting type silicone, followed by setting it with ultraviolet ray, to provide the separator of the present invention.

EXAMPLE 3

A 4-layer plastic film (thickness 30 $\mu$m) composed of a polymer blend layer (thickness 5 $\mu$m) composed of 10% by weight polyethylene, 20% by weight an ethylene-vinyl acetate copolymer, 10% by weight EPDM, and 60% by weight polypropylene as a 1st layer, the surface of which was a matte surface, an ethylene-methyl methacrylate copolymer single layer (thickness 10 $\mu$m) as a 2nd layer, a polypropylene single layer (thickness 10 $\mu$m) as a 3rd layer, and the same polymer blend layer as the 1st layer as a 4th layer, the surface of which was also a matte surface was prepared to provide the separator of the present invention. The surface roughness of the matte surfaces each was 4 $\mu$m.

EXAMPLE 4

A double layer plastic film (thickness 15 $\mu$m) composed of a 1st layer same as 1st layer having the matte surface as in Example 1 and a polyester layer (thickness 10 $\mu$m) as a 2nd layer was prepared to provide the separator of the present invention.

COMPARATIVE EXAMPLE 1

By coating a plastic film of 50 $\mu$m in thickness composed of 100% by weight low-density polyethylene with the

COMPARATIVE EXAMPLE 2

By coating a plastic film of 25 $\mu$m in thickness composed of 100% by weight polypropylene with the same silicone as in Example 1, a separator was prepared.

The characteristics of each of the separators obtained were evaluated by the following methods and the results obtained are shown in Table 1 below.

1. Surface Roughness

The central line average roughness Ra defined by JIS B 0601-1982 was used.

2. Static Friction Coefficient and Kinetic Friction Coefficient

The friction coefficients were measured using a test sample of 50 mm×50 mm, a stainless steel (SUS 304A) material to be contacted and a 500 g sliding piece at a test speed of 300 mm/minute according to JIS K-7125.

3. Sound Pressure

The sound pressures at tearing each sample and at crushing each sample were measured by the following methods using an A level precise noise meter at a distance of 100 mm from the sound source.

(1) At Tearing

A notch was formed at the center portion of a sample of 100 mm×100 mm, the sample was torn upward and downward from the notch at about 300 mm/minute, and the sound pressure at the case was measured.

(2) At Crushing (Ring method)

Two samples each having an area of 100 mm×100 mm were superposed each other, a ring was formed by the superposed samples, and the sound pressure at crushing the ring from above at about 300 mm/minute was measured.

(3) At Crumpling With Hands

Two samples each having an area of 100 mm×100 mm were superposed each other and the sound pressure at crumpling with hands was measured.

4. Softness

Each sample was touched by 10 persons and the feeling was evaluated by the following standard.

A: Evaluated as good by 7 to 10 persons.
B: Evaluated as good by 3 to 6 persons.
C: Evaluated as good by 2 or less persons.

TABLE 1

| Example No. | Static Friction Coefficient | Kinetic Friction Coefficient | Sound Pressure* (dB) (A) | (B) | (C) | Softness |
| --- | --- | --- | --- | --- | --- | --- |
| Example 1 | 0.6 | 0.4 | 65 | 66 | 68 | A |
| Example 2 | 0.4 | 0.3 | 62 | 64 | 68 | A |
| Example 3 | 0.5 | 0.3 | 62 | 63 | 70 | A |
| Example 4 | 0.5 | 0.4 | 78 | 76 | 77 | A |
| Comparative Example 1 | 1.5 | 1.3 | 83 | 82 | 93 | B |
| Comparative Example 2 | 1.5 | 1.2 | 90 | 88 | 95 | C |

*) (A): At tearing
(B): At crushing
(C): At crumpling with hands

The separator or the packaging material of the present invention has a proper softness and a nerve, and shows a low surface friction coefficient, whereby the productivity at the production of the articles such as pressure-sensitive adhesive articles and sanitary articles is improved as well as the commercial value is very excellent since the sound thereof at use can be lowered and the product has a soft feeling.

While the invention has been described in detail with reference to specific embodiments, it will be apparent to one skilled in the art that various changes and modifications can be made to the invention without departing from its spirit and scope.

What is claimed is:

1. A package and sanitary napkin combination comprising:

(1) a sanitary napkin having on a surface thereof a pressure-sensitive adhesive layer for affixing the napkin to an undergarmnent, packaged in (2) a packaging material comprising a thermoplastic plastic film from 20 to 40 μm in thickness having an outer surface which is a matte or embossed surface with a surface roughness (Ra) not greater than ½ the thickness of the film and having an inner surface coated on at least a part thereof with a release treatment layer selected from the group consisting of an ultraviolet setting silicone treatment layer and an electron ray setting silicone treatment layer, said release treatment layer being removably adhered to the pressure-sensitive adhesive layer on the napkin;

wherein the inner surface of the film is a matte or embossed surface with a surface roughness (Ra) of from 2 to 10 μm and not greater than ½ the thickness of the film, and the static and kinetic friction coefficients of the release treated matte or embossed inner surface are less than 1.5 and 1.2, respectively.

2. A package, separator and sanitary napkin combination comprising:

(1) a sanitary napkin having on a surface thereof a pressure-sensitive adhesive layer for affixing the napkin to an undergarment, and (2) a separator comprising a thermoplastic plastic film from 20 to 40 μm in thickness having an outer surface which is a matte or embossed surface with a surface roughness (Ra) not greater than ½ the thickness of the film and having an inner surface coated on at least a part thereof with a release treatment layer selected from the group consisting of an ultraviolet setting silicone treatment layer and an electron ray setting silicone treatment layer, said release treatment layer being removably adhered to the pressure-sensitive adhesive layer on the napkin, packaged in (3) a plastic wrap package;

wherein the inner surface of the film is a matte or embossed surface with a surface roughness (Ra) of from 2 to 10 μm and not greater than ½ the thickness of the film, and the static and kinetic friction coefficients of the release treated matte or embossed inner surface are less than 1.5 and 1.2, respectively.

3. A package, separator and sanitary napkin combination comprising in this order:

(1) a sanitary napkin having on a surface thereof a pressure-sensitive adhesive layer for affixing the napkin to an undergarment, (2) a separator comprising a thermoplastic plastic film from 20 to 40 μm in thickness having (a) an inner surface which is a matte or embossed surface with a surface roughness (Ra) of from 2 to 10 μm and not greater than ½ the thickness of the film, coated on at least a part thereof with a release treatment layer selected from the group consisting of an ultraviolet setting silicone treatment layer and an electron ray setting silicone treatment layer, said release treatment layer being removably adhered to the pressure sensitive adhesive layer on the napkin, and (b) an outer surface, (3) a pressure-sensitive adhesive layer having an inner surface adhered to at least a part of the outer surface of the separator, and an outer surface, and (4) a plastic wrap package adhered to the outer surface of the pressure-sensitive adhesive layer and enclosing the napkin;

wherein the static and kinetic friction coefficients of the release treated matte or embossed surface are less than 1.5 and 1.2, respectively.

4. The combination of claim 1, wherein the surface roughness (Ra) of the outer surface is 25 μm or less.

5. The combination of claim 2, wherein the surface roughness (Ra) of the outer surface is 25 μm or less.

6. The combination of claim 1, wherein the thermoplastic plastic film is a single layer polymer film composed of a polymer blend.

7. The combination of claim 2, wherein the thermoplastic plastic film is a single layer polymer film composed of a polymer blend.

8. The combination of claim 3, wherein the thermoplastic plastic film is a single layer polymer film composed of a polymer blend.

9. The combination of claim 6, wherein the polymer blend is a blend of at least two polymers selected from the group consisting of polyethylene, polypropylene, ethylene-vinyl acetate copolymers, ethylene-(meta)acrylic acid copolymers, ethylene-methyl (meta)acrylate copolymers, ethylene-ethyl (meta)acrylate copolymers, polyethylene-propylene copolymers, olefinic elastomers, styrenic elastomers, polyisobutylene, and butyl rubber.

10. The combination of claim 7, wherein the polymer blend is a blend of at least two polymers selected from the group consisting of polyethylene, polypropylene, ethylene-vinyl acetate copolymers, ethylene-(meta)acrylic acid copolymers, ethylene-methyl (meta)acrylate copolymers, ethylene-ethyl (meta)acrylate copolymers, polyethylene-propylene copolymers, olefinic elastomers, styrenic elastomers, polyisobutylene, and butyl rubber.

11. The combination of claim 8, wherein the polymer blend is a blend of at least two polymers selected from the group consisting of polyethylene, polypropylene, ethylene-vinyl acetate copolymers, ethylene-(meta)acrylic acid copolymers, ethylene-methyl (meta)acrylate copolymers, ethylene-ethyl (meta)acrylate copolymers, polyethylene-propylene copolymers, olefinic elastomers, styrenic elastomers, polyisobutylene, and butyl rubber.

12. The combination of claim 1, wherein the thermoplastic film is a multilayer polymer film and the outer layer having the matte or embossed surface is composed of a polymer blend.

13. The combination of claim 2, wherein the thermoplastic film is a multilayer polymer film and the outer layer having the matte or embossed surface is composed of a polymer blend.

14. The combination of claim 3, wherein the thermoplastic plastic film is a multilayer polymer film and the inner layer having the matte or embossed surface is composed of a polymer blend.

* * * * *